United States Patent [19]

Hansen et al.

[11] 4,383,218
[45] May 10, 1983

[54] EDDY CURRENT FLOW DETECTION INCLUDING COMPENSATION FOR SYSTEM VARIABLES SUCH AS LIFT-OFF

[75] Inventors: Karl A. Hansen; Iver G. Hendrickson, both of Seattle, Wash.

[73] Assignee: The Boeing Company, Seattle, Wash.

[21] Appl. No.: 192,251

[22] Filed: Sep. 30, 1980

Related U.S. Application Data

[63] Continuation-in-part of Ser. No. 974,356, Dec. 29, 1978, Pat. No. 4,271,393.

[51] Int. Cl.³ .................... G01N 27/90; G01R 33/12
[52] U.S. Cl. ..................................... 324/225; 324/240
[58] Field of Search ............... 324/202, 225, 228, 229, 324/240, 239

[56] References Cited

U.S. PATENT DOCUMENTS

| | | | |
|---|---|---|---|
| 2,965,840 | 12/1960 | Renken, Jr. et al. | 324/37 |
| 3,197,693 | 7/1965 | Libby | 324/225 |
| 3,229,197 | 1/1966 | Renken, Jr. | 324/40 |
| 3,654,446 | 4/1972 | Gordon et al. | 235/151.3 |
| 3,908,118 | 9/1975 | Micka | 235/181 |
| 3,974,442 | 8/1976 | Savidge et al. | 324/37 |
| 4,005,281 | 1/1977 | Faulhaber et al. | 235/151.3 |
| 4,005,601 | 2/1977 | Botello | 73/146 |
| 4,031,630 | 6/1977 | Fowler | 33/356 |
| 4,053,748 | 10/1977 | Kueppers | 364/525 |
| 4,064,452 | 12/1977 | Toth | 324/202 |
| 4,074,186 | 2/1978 | Flaherty | 324/222 |
| 4,079,237 | 3/1978 | Schlesinger | 364/563 |
| 4,079,312 | 3/1978 | Osborn et al. | 324/226 |
| 4,087,749 | 5/1978 | McCormack | 324/225 |
| 4,089,054 | 5/1978 | Ott | 364/527 |
| 4,091,543 | 5/1978 | Lapeyre | 33/356 |
| 4,099,240 | 7/1978 | Rode et al. | 364/571 |
| 4,271,393 | 6/1981 | Hansen et al. | 324/240 |
| 4,274,054 | 6/1981 | Savidge et al. | 324/225 |
| 4,331,920 | 5/1982 | Kalisch et al. | 324/225 |

OTHER PUBLICATIONS

Calibration of Eddy Current Systems with Simulated Signals, J. C. Crowe, 9/77–*Materials Evaluation*, pp. 59–64.

*Primary Examiner*—Gerard R. Strecker
*Attorney, Agent, or Firm*—Christensen, O'Connor, Johnson & Kindness

[57] ABSTRACT

Disclosed is an eddy current inspection system for nondestructive detection of subsurface flaws in regions of multilayer conductive structure that surround a fastener which joins the conductive layers. The eddy currents are induced by an aperiodic drive current having a relatively long rise time and a relatively last fall time that is supplied to a drive coil and a pick-up coil that is mounted with the drive coil supplies a signal representative of the induced eddy currents. Compensation is provided for variation in lift-off (spacing between the surface of the structure being inspected and the surface of the drive coil and pick-up) by utilizing parametric relationships relative to the maximum amplitude of inspection signals supplied when subsurface flaws exist and inspection signals supplied when lift-off is present. Because similar parametric relationships exist relative to other system characteristics that affect the electromagnetic environment of the inspection media, compensation can also be provided for variation in the height of fasteners (protrusion), fastener edge margin, and gaps or spacing between the successive conductive layers of the multilayer structure. By utilizing a microprocessor or other sequential digital signal processing apparatus, values that define the parametric relationships utilized in compensating for any particular system characteristic can be stored in memory for the inspection of a relatively large number of structural configurations.

8 Claims, 6 Drawing Figures

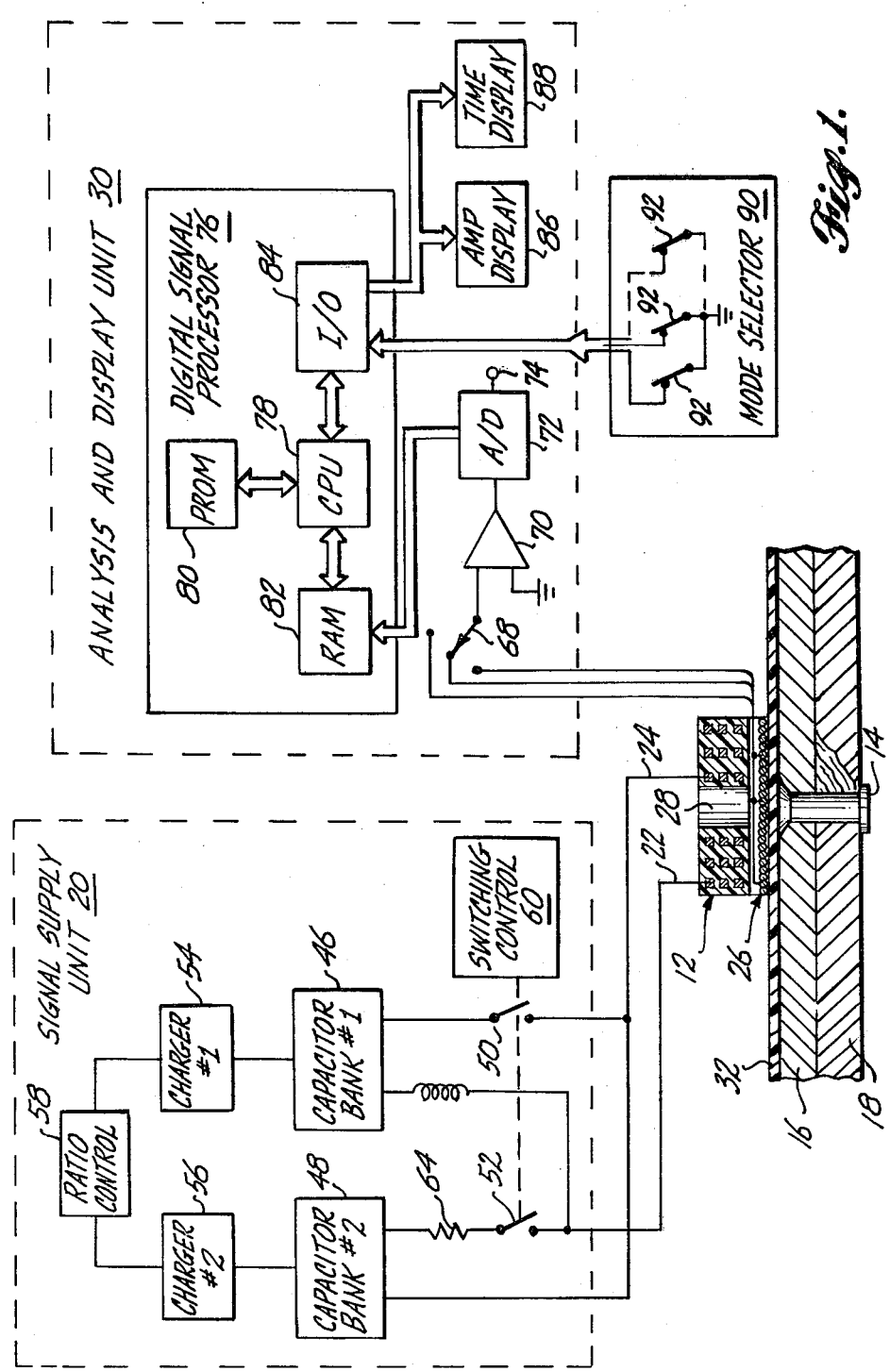

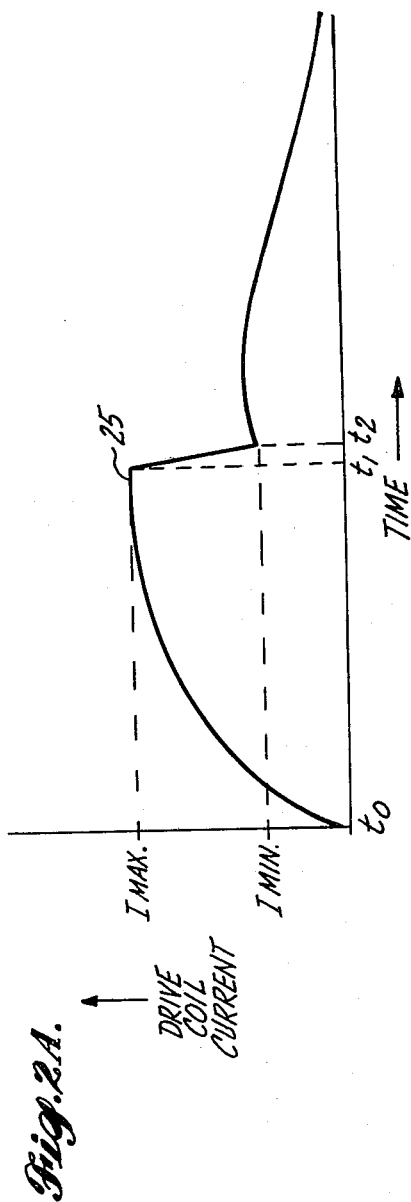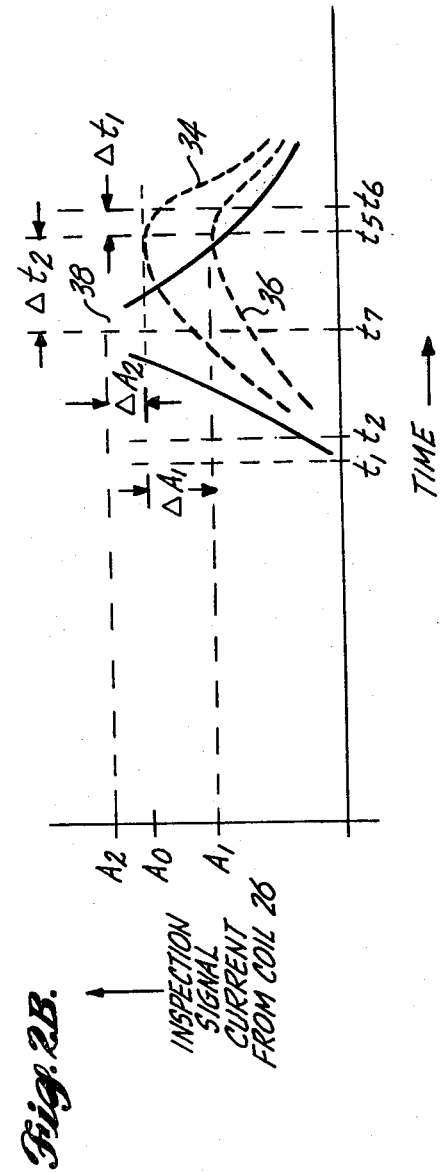

EDDY CURRENT FLOW DETECTION INCLUDING COMPENSATION FOR SYSTEM VARIABLES SUCH AS LIFT-OFF

RELATED APPLICATIONS

This application is a continuation-in-part of application Ser. No. 974,356, filed Dec. 29, 1978 (now U.S. Pat. No. 4,271,393).

BACKGROUND OF THE INVENTION

This invention relates to methods and apparatus for the use of eddy currents to detect subsurface discontinuities in metal objects. This invention is particularly directed to methods and apparatus for detecting cracks and flaws within multilayer conductive structure that is joined together by fasteners that extend through each structural layer.

Copending U.S. patent application Ser. No. 974,356, which was filed Dec. 29, 1978 and is assigned to the same assignee as this application (now U.S. Pat. No. 4,271,393), discloses nondestructive inspection of conductive bodies and structure wherein eddy currents are induced in the conductive structure by means of an excitation coil that is placed in abutment with the structure to be examined and driven with a current pulse that increases at a relatively slow rate and, upon reaching a predetermined level, decreases at a relatively rapid rate. Driven in such a manner, the excitation coil supplies a corresponding aperiodic magnetic field that penetrates the conductive material being examined during the relatively slow build-up period and produces substantial eddy currents throughout the affected conductive region as the field rapidly collapses.

To detect subsurface discontinuities, including cracks and other flaws, the composite magnetic field (which results from the interaction of the energization field and the magnetic field produced by the induced eddy currents) is detected by a sensing coil (or other magnetic flux detector) and the resulting electrical signal is compared with a signal obtained when an identically configured, flaw-free structure (i.e., a reference specimen) is electromagnetically excited in the same manner. In particular, the referenced patent application dicloses the use of a storage-type oscilloscope for simultaneous display of the electrical signal produced by the sensing coil when eddy currents are produced within the flaw free reference structure and the signal produced when eddy currents are induced in the structure being inspected.

One important aspect of eddy current inspection apparatus of the type disclosed in the above-referenced patent application is that the initial portion of the signal supplied by the sensing coil during each inspection sequence is primarily determined by structural features and discontinuities that lie in or near the surface of the conductive region being examined whereas later portions of the signal are more indicative of discontinuities that lie relatively deep within the conductive material. Accordingly, by disregarding or eliminating initial portions of the signal supplied by the sensing coil, an eddy current inspection system of the type disclosed in the above-referenced patent application can be made relatively insensitive to discontinuities in the surface of the material being inspected, including design features such as the edge of the top conductive member in a multilayer structure as well as machined apertures such as countersink and counterbore regions.

The above-discussed eddy current inspection technique provides several other advantages over previously employed eddy current inspection arrangements, which generally employ a continuous-wave (CW) electrical signal to produce the time-varying magnetic field that induces eddy currents within the material being examined. For example, as is discussed in more detail in the previously-referenced patent application, improvement of approximately one order of magnitude is obtained relative to system sensitivity or resolution in that cracks on the order of 0.2 inches in length that lie as deep as 0.5 inches below the surface of the material can be detected by utilizing an aperiodic energization signal in the disclosed manner. Further, since such a technique results in substantially lower power dissipation within the excitation coil, relatively small excitation coils can be utilized and thermal drift often encountered in systems employing a CW excitation current is eliminated. Since smaller coils can be used, a system of this type can also examine a smaller region of a conductive structure and, hence, provide improved resolution as to determining both the position and size of a subsurface crack or flaw.

Because of these and other advantages, the method and apparatus disclosed in the referenced U.S. patent application is especially advantageous in the more demanding situations such as those which require the detection of subsurface flaws in conductive material which includes various intended surface features. For example, the disclosed embodiments of the referenced patent application are configured for the inspection of multilayer conductive structure that is joined together by the use of various conventional fasteners such as rivets or bolts, with assemblies such as those utilized in modern high speed aircraft being of special significance. In this regard, in the manufacture and maintenance of aircraft and other structural assemblies that are subjected to substantial mechanical stress or strain through vibration or other physical forces, it is often necessary and desirable to detect fatigue-induced cracks or flaws that can develop in a subsurface layer, especially along the periphery of a fastener which joins such a subsurface layer to other conductive layers or various frame members.

Although offering significant advantages over prior art eddy current inspection apparatus such as those employing CW excitation signals, the method and apparatus disclosed in our previously-referenced patent application do not completely overcome all of the problems associated with the inspection of multilayer conductive structure such as that employed in aircraft and other important arrangements which present a complex electromagnetic environment that varies from one test situation to the next. In this regard, the exact nature of the induced eddy currents and hence the electrical signal supplied by the sensing coil of an eddy current inspection apparatus not only depends on the location and configuration of subsurface discontinuities such as cracks or other flaws, but is significantly affected by the structural arrangement of interest; by the magnetic and electrical properties of the materials involved; and by other factors such as the position of the excitation and sensing coils relative to the structure being examined. More specifically, even though the presence of subsurface flaws and discontinuities is determined by comparing the electrical signal produced by the sensing coil when eddy currents are produced in a flaw-free reference structure with the signal produced when an identical excitation signal is used to induce eddy currents in the structure being inspected, variations in structural arrangement and material properties that are acceptable from a manufacturing standpoint can produce fairly significant differences in the characteristics of the signal provided the sensing coil, including changes in maximum signal amplitude and the relative time between initiation of the excitation signal and the time at which the signal reaches maximum amplitude. For example, in inspecting regions of a multilayer structure that surround fasteners for fatigue-induced cracks, allowable deviation of the inspected arrangement from design value with respect to edge margin, fastener countersink configuration (including the flushness of the fastener head relative to the surface of the structure), variation in the thickness of each conductive layer and variation in the conductivity and permeability of either the fastener or one or more of the conductive layers affect the induced eddy currents and hence cause variation in the test results. Moreover, factors that are not generally controlled during the manufacture of aircraft and other such structure can substantially alter the electromagnetic environment presented by the structure being inspected and thus alter the signal supplied by the sensing coil. For example, it is common practice to coat various portions of aircraft with paint or other protective material. Since such coatings are generally nonconductive, the excitation coil is, in effect, electromagnetically spaced apart from the structure being examined, even though physical contact is maintained between the coil and the coated surface of the structure being examined. In addition, a test set operator may fail to maintain the excitation coil in full abutment with the structure under test during the inspection routine and hence introduce additional variation in the electromagnetic configuration relative to that presented by the reference specimen. Because the thickness and dielectric constant of a protective coating such as paint is not generally controlled during manufacture or maintained relatively constant during the lifetime of an aircraft or other structure the reference structure cannot generally be configured to present an electromagnetic environment substantially identical to that of the inspected conductive region.

Each factor that affects the electromagnetic characteristics of the structure being examined and varies as a function of manufacturing tolerances and material properties or as a function of uncontrolled parameters (e.g., the thickness of a protective surface coating or the positioning of the test apparatus coils) in effect decreases inspection system sensitivity and resolution relative to that which can be attained under optimal conditions. Thus, although the methods and apparatus of our previously referenced patent application provide substantial advantages over prior art CW eddy current inspection techniques, it has still been necessary to rely on the expertise of the system operator to properly interpret and analyze some of the inspection signals so as to differentiate between acceptable variations in one or more of the inspection parameters and the presence of a subsurface crack or flaw.

In addition to the fact that the method and apparatus disclosed in our above-referenced patent application do not provide optimum results relative to the information contained in the signal provided by the system sensing coil, the embodiments of eddy current inspection apparatus disclosed therein are not ideally arranged relative to use in typical production and maintenance shop environments or by personnel of typical training and ability. For example, the use of a storage-type oscilloscope for displaying the signal supplied by the sensing coil when eddy currents are produced within a flaw-free reference specimen and the signal produced when eddy currents are induced in the structure being inspected may be satisfactory when highly trained technical personnel are practicing the invention in a test laboratory, but may be unacceptable when production or maintenance personnel are attempting to locate subsurface cracks and flaws in aircraft that are located in a factory or on a flight line. Further, modern aircraft and other similar structure include an extremely large number of fastener configurations which vary as to fastener type and size as well as to the physical arrangement and properties of the joined-together conductive structure. Thus, even if eddy current inspection is utilized only with respect to those fasteners that are located in portions of the aircraft that are exposed to substantial vibration or other forces practicing the eddy current inspection scheme in the manner disclosed in our copending patent application can require a large number of reference specimens which must be transported to the inspection site and stored when not in use.

Accordingly, it is an object of this invention to provide methods and apparatus for eddy current inspection of conductive structure wherein compensation is effected relative to selected spatial, structural, and/or material characteristics that have previously affected the results of such inspection techniques.

It is another object of this invention to provide improvements in the eddy current inspection methods and apparatus disclosed in the previously-referenced copending patent application; such improvements providing improved interpretation of inspection signals provided to thereby at least partially eliminate test uncertainties resulting from otherwise acceptable variations in various parameters that affect electrical and magnetic properties of the structure being inspected.

It is still another object of this invention to provide methods and apparatus for eddy current detection of subsurface cracks and flaws in multilayer conductive structure such as the structure employed in aircraft with compensation being provided for the effect of one or more factors that affect the electromagnetic characteristics of the structure.

It is yet another object of this invention to provide methods and apparatus of the above-described nature for detecting fatigue-induced cracks about the periphery of fasteners that join one or more conductive layers or panels to additional panels or frame members with compensation being provided relative to uncontrolled variations in the spatial relationship between the test apparatus and the structure under test; such variations resulting from dielectric coatings or other factors.

Even further, it is an object of this invention to provide eddy current apparatus of the above-mentioned type which is configured and arranged to facilitate inspection of a relatively large number of fastener regions and is adapted for use by production and maintenance personnel in typical production and maintenance environments.

SUMMARY OF THE INVENTION

These and other objects are achieved in accordance with this invention by utilizing the parametric relationships that exist between the amplitude and time characteristics of the system inspection signal relative to variations in one or more structural or test parameters that affect the electromagnetic properties of the structure under test or the spatial relationship between the test apparatus and such structure. These parameters include separation between the inspection coil and the structure under test (i.e., lift-off); the magnitude of any spacing or gap between adjacent layers of the structure; fastener edge margin; and fastener protrusion above the top surface of the structure. In this regard, it has been discovered that the relationship between the maximum amplitude of signals produced by the sensing coil of a system configured in accordance with previously-referenced patent application Ser. No. 974,356, and the time at which such a signal reaches maximum amplitude is substantially linear if the size of the subsurface flaw (e.g., a fatigue-induced crack) that radiates outwardly from a fastener is the only inspection variable (i.e., all other variables that affect the electromagnetic properties of the system are constant). That is, an electrical signal that is obtained when a particularly configured fastener region of a multilayer conductive surface having variously dimensioned subsurface flaws is electromagnetically excited in accordance with the invention substantially corresponds to a point on a line $A = A_0 + mT$, where the variable A denotes the maximum amplitude of the signal that results from the subject inspection procedure, T represents the time at which maximum signal amplitude is attained, $A_0$ and m are rational real numbers that characterize the particular structure being inspected and the exact point defined depends on the relative size of the subsurface crack or flaw. In conjunction with this it has been found that substantially different linear amplitude-time characteristics exist when lift-off (or any one of several other important inspection parameters such as certain fastener edge margins, spacing between adjacent conductive layers and fastener height or protrusion) is the only system variable. In accordance with this invention, the linear parametric relationship that is associated with structure including discontinuities of various size and the linear parametric relationship associated with a flaw-free specimen in which the only system variable is lift-off (or some other factor that adversely affects system performance) is determined prior to inspection of one or more similarly configured fastener regions that may or may not present lift-off, a subsurface flaw, or both. During inspection of the "unknown" structure, each signal supplied by the sensing coil is modified on the basis of the time and amplitude characteristics of the test signal and the two above-mentioned parametric relationships so as to at least partially eliminate the signal component resulting from that amount of lift-off that is present in each particular test sequence.

In accordance with the disclosed embodiments of the invention, the two above-discussed parametric relationships that are required are determined on the basis of at least three inspection sequences utilizing specifically configured reference specimens. More specifically, the maximum amplitude and time at which such amplitude is attained is determined for: (1) a flaw-free reference structure that exhibits the nominal design features of the fastener region to be inspected; (2) at least one substantially identically configured structure that includes a crack or flaw; and, (3) at least one substantially identically configured flaw-free reference structure arranged to exhibit lift-off or another undesirable inspection characteristic for which compensation is desired or necessary. Since the amplitude and time associated with the flaw-free reference specimen which does not include lift-off necessarily defines the intersection of the two above-discussed straight lines and the time and amplitude information associated with each of the two other reference inspection sequences correspond to a point on each of the two straight lines, the two desired parametric relationships for that particular structural arrangement are completely defined, and various signal processing can be employed to provide the desired compensation of subsequent inspection signals. In this regard, in one disclosed embodiment of the invention, signal processing is employed that, in effect, transforms the maximum amplitude and time characteristic of the signal associated with the flaw-free, lift-off free inspection signal so that it corresponds to the origin in a two-dimensional amplitude-time coordinate system and determines the slope of the lines defined by the two linear parametric relationships of interest. Utilizing this technique, only two parameters are required to describe both straight line segments (i.e., the slope of each of the two straight lines relative to the transformed coordinate system).

Regardless of the number of reference specimens utilized to determine the exact parametric relationship that applies to a given structural configuration of interest and whether slope or some other parameter is used to define the relationships, the signal associated with each subsequently inspected structural arrangement is compensated by, in effect, determining the point at which a line that is parallel to the line defined by the parametric relationship associated with lift-off intersects the line defined by the parametric relationship associated with structure that includes a subsurface crack or flaw. In this regard, it has been determined that the amplitude associated with this intersection is generally a sufficient indication of whether or not a subsurface crack or flaw is present. Thus, embodiments of the invention need not be configured for determining and displaying both the amplitude and time associated with the compensated inspection signal, but need only include signal processing and display provision relative to the amplitude component.

In the disclosed embodiments of the invention, the signal analysis necessary to determine the applicable parametric relationships and the compensated inspection value for each unknown structure that is examined is implemented with digital signal processing techniques. More specifically, each disclosed embodiment of the invention includes an analog-to-digital (A/D) converter for supplying a sampled-data representation of the signal supplied by the inspection system sensing coil with the parallel-format digital signal provided by the A/D converter being coupled to a microprocessor or other suitable sequential logic arrangement. Mode selector switches, which control the sequencing of the microprocessor, facilitate storage of the parametric values associated with each structural configuration to be inspected. For example, the disclosed arrangements can be operated so that the slopes of the two previously-discussed amplitude-time relationships are determined by the digital processor (e.g., microprocessor) and stored in a programmable read-only memory as the test sequences necessary to determine the relationships are being performed. Alternatively, if desired or necessary, the applicable parametric relationships can be entered into the inspection system memory from previously-prepared lists or tables. When the system is utilized for detecting subsurface cracks and flaws in similarly configured structure, the microprocessor determines the time and magnitude associated with the resulting inspection signal and, based on the stored reference information, determines and displays the compensated system signal.

Since relatively few parameter values are required to completely define each particular structural arrangement (e.g., the two above-discussed slope values, embodiments of the invention can be programmed for the inspection of a relatively large number of fastener configurations. Further, the reference structure need not be taken to the actual inspection site, unless desired. Thus, production line and flight line testing is facilitated.

BRIEF DESCRIPTION OF THE DRAWING

These and other features and advantages of the present invention will become apparent to one skilled in the art after reading the following description taken together with the accompanying drawing, in which:

FIG. 1 is a block diagram representation of an eddy current inspection system configured in accordance with this invention which illustrates use of the invention to detect cracks or flaws in a subsurface layer of a multilayered conductive structure;

FIGS. 2A and 2B respectively depict a typical current pulse utilized to establish the magnetic field that induces eddy currents in the inspected structure and typical signals supplied by the inspection system sensing coil;

DETAILED DESCRIPTION

Figure 3:
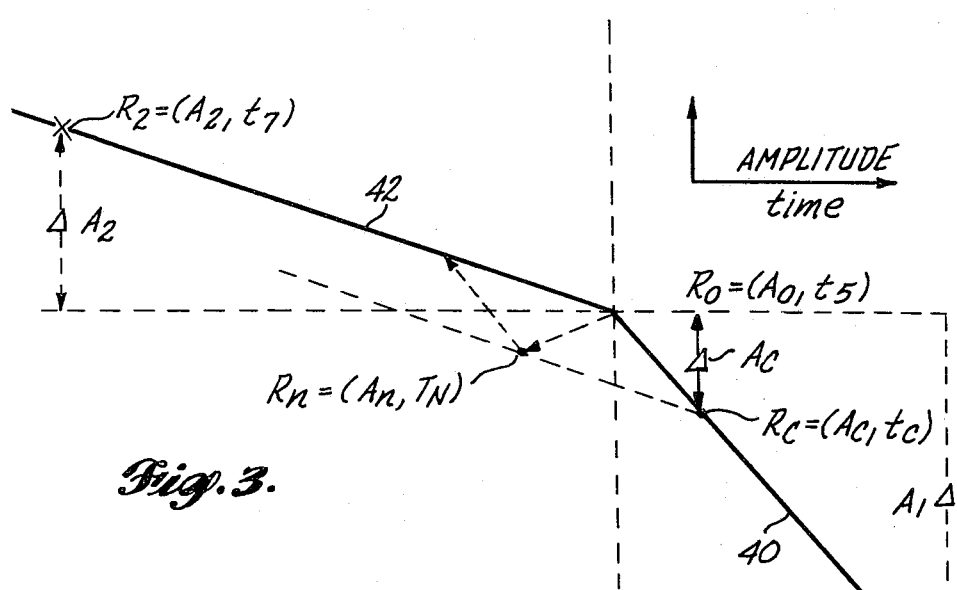
FIG. 3 graphically depicts two linear amplitude-time characteristics associated with the inspection of a typical multilayer fastener arrangement when lift-off and size of a subsurface crack, are the only system variables.

FIG. 1 diagrammatically illustrates a basic embodiment of this invention which is arranged for detecting subsurface flaws within multilayered conductive structures by inducing eddy currents in the structure being inspected and for providing compensation relative to variations in one or more characteristics that affect the electromagnetic environment of the inspection arrangement and, hence, the inspection results. More specifically, the inspection system of FIG. 1 is arranged for the detection of fatigue-induced cracks or other discontinuities in subsurface regions that surround conventional fasteners such as rivets or bolts that join two or more sheets of conductive material, interconnect one or more conductive layers to other structures such as frame members, or join two adjacent surface sheets to a conductive plate so as to form a conventional joint or splice with the detection of such discontinuities being detected on the basis of perturbations in induced eddy currents which result because such flaws alter the amplitude and signal path of the eddy currents. Since a variation in substantially any parameter of the inspection arrangement which alters an electrical or magnetic property causes at least some change in the induced eddy currents, the inspection system of FIG. 1 is configured to automatically compensate for changes in one or more such inspection parameters. In this regard, although the embodiments described herein are primarily discussed in terms of compensating for variations in lift-off (i.e., variations in the spacing between the surface of the structure being inspected and the two electrical coils which provide the eddy current-inducing electromagnetic field and sense the composite electromagnetic field to detect perturbations in the eddy currents), it will be recognized upon fully understanding the invention that the methods and apparatus disclosed herein may be utilized to compensate for other eddy current inspection system variables that may be more important than lift-off when such a system is adapted to inspect various specific structural arrangements. Further, upon fully understanding the embodiments disclosed herein, those skilled in the art will recognize that the practice of the invention is not limited to the specific inspection situations discussed, but can be utilized in a variety of situations wherein electrically conductive objects are to be examined for the presence and/or location of subsurface discontinuities, voids, or flaws. In this regard, the invention can be used to locate virtually any subsurface feature having an electrical conductivity that is less than that of the normal conductivity of the object being examined. Thus, for example, the presence and location of various internal openings can be determined within virtually any object that is constructed of conductive material.

With more particular reference to FIG. 1, the depicted embodiment of the invention includes a drive coil 12 that is symmetrically positioned over a fastener 14 which structurally joins an electrically conductive surface sheet 16 with an electrically conductive bottom sheet 18. Energization current for drive coil 12, consisting of a single pulse of current having a relatively long rise time and a relatively short fall time, is supplied by a signal supply unit 20 that is interconnected with drive coil 12 by means of electrical conductors 22 and 24. This current, which substantially corresponds to the waveform 25 shown in FIG. 2A, causes drive coil 12 to establish a magnetic field having lines of flux that penetrate into the adjoining region of surface sheet 16 and bottom sheet 18 during the slowly rising portion of the current pulse (time $t_0$ to $t_1$ in FIG. 2A) and produces substantial eddy currents that flow circumferentially about fastener 14 as the current pulse and associated magnetic flux rapidly decays in magnitude (time $t_1$ to $t_2$ in FIG. 2A). These eddy currents, in effect, establish an additional electromagnetic field which interacts with the electromagnetic field produced by drive coil 12. Since the exact paths followed by the eddy currents depend on the conductivity of portions of surface sheet 16 and bottom sheet 18 that surround fastener 14, flaws or other discontinuities within such regions alter the eddy current flow relative to that exhibited when a flaw-free fastener region of substantially identical configuration is subjected to a substantially identical electromagnetic field.

In practicing the invention, a multilayer solenoidal coil is preferably utilized as drive coil 12. For example, a coil having approximately sixty turns that is wound in four layers with an inside diameter of 0.75 inches (1.91 centimeters), and an outside diameter of 1.5 inches (3.81 centimeters) and a height of 1.5 inches (3.81 centimeters) so as to exhibit an inductance of approximately twenty microhenries and a resistance of approximately four milliohms has been satisfactorily utilized in various embodiments of the invention. In this regard, although other types of low inductance coils can be employed, including the spirally wound "pancake" coils discussed in our copending patent application, Ser. No. 974,356, filed Dec. 29, 1978, solenoidal coils are advantageous in that the lines of magnetic flux produced by such a coil are substantially parallel to the axial centerline of the coil, even at or near each annular end face of the coil. Thus, solenoidal coils produce a magnetic field having lines of flux that are substantially perpendicular to the surface sheet 16, a feature which tends to reduce sensitivity of the inspection system to minor variations in surface configurations such as the depth of the fastener countersink or contour of the surrounding conductive region.

It should be noted that our previously-referenced patent application includes a description of a basic eddy current inspection system that utilizes a periodic excitation current. Although the following paragraphs contain information essential to practicing the present invention, the disclosure of our referenced copending application is incorporated herein by reference.

To detect the electromagnetic field produced by the combined effect of drive coil 12 and the resulting eddy currents, the arrangement of FIG. 1 includes a relatively flat, spirally wound "pancake" pick-up coil 26 that is mounted to the lower face of drive coil 12 and, hence, positioned directly above fastener 14 of the region being inspected. Alternatively, pick-up coil 26 can be mounted within the lower portion of the central opening 28 of drive coil 12 if sufficient space is available. For example, in one embodiment of the invention that employs a drive coil 12 wherein the diameter of central opening 28 is 0.75 inches (1.91 centimeters), a single layer, spirally wound pancake coil having approximately twenty turns and a diameter of 0.75 inches is mounted to fully occupy the lower portion of central opening 28. Regardless of whether pick-up coil 26 is mounted within the opening 28 or is positioned adjacent the lower face of drive coil 12, both drive coil 12 and pick-up coil 26 are preferably encapsulated in a dielectric material such as a thermoplastic resin to, in effect, form a unitary structure that can be easily positioned over each fastener 14 of the conductive structure under test. Encapsulation of drive coil 12 and pick-up coil 26 also maintains constant spatial relationship between the two coils even though substantial mechanical force is exerted on the coils. More specifically, in the practice of the invention, current pulses having a maximum amplitude ($I_{max}$ in FIG. 2A) of between 100 and 1,000 amperes are utilized with the change in current that induces the eddy currents ($I_{max}$-$I_{min}$ in FIG. 2A) ranging between approximately 100 and 50 percent of $I_{max}$.

As is also diagrammatically depicted in FIG. 1, a tapped coil arrangement can be utilized as pick-up coil 26 to thereby permit controlling the effective diameter of the pick-up coil. This enables use of a relatively small diameter pick-up coil when inspecting conductive regions that utilize fasteners 14 constructed of steel or other high permeability material wherein the magnetic flux is concentrated within and closely adjacent to the fastener. In addition, it can be advantageous to use a relatively small pick-up coil in situations in which the boundary edge of surface sheet 16 is located in close proximity to fastener 14 (i.e., minimal fastener edge margin is present), since such a boundary edge can effect the configuration of the induced electromagnetic field. When a tapped coil is utilized as pick-up coil 26, each of the above-mentioned situations can be facilitated by selecting an electrical tap which provides an appropriate effective coil diameter. It should be noted that, although a tapped configuration need not be employed as pick-up coil 26, spirally wound, pancake-type coils are currently preferred over other types of electrical coils and other magnetic flux sensors such as Hall Effect devices (at least in the embodiments in the invention employing a solenoidal drive coil 12) because such an arrangement minimizes magnetic coupling between drive coil 12 and pick-up coil 26. That is, relatively flat, spirally wound pick-up coils exhibit maximum sensitivity to time-varying magnetic fields having lines of flux substantially parallel to the plane of the coil. Thus, the major flux component of the electromagnetic field produced by solenoidal coil 12 of FIG. 1 is substantially orthogonal to the plane of maximum sensitivity of pick-up coil 26 and magnetic coupling between drive coil 12 and pick-up coil 26 is minimized.

Regardless of the exact structure employed for drive coil 12 and pick-up coil 26, an inspection signal representative of the electromagnetic field produced by each inspection procedure is coupled to an analysis and display unit 30, which is arranged to compare each inspection signal information associated with a particular fastener region under test with reference data that pertains to a flaw-free, identical structure and to compare each inspection signal with signal information that pertains to identically configured structure that includes subsurface cracks. In this respect, it has been discovered that the use of such reference data can improve inspection system results relative to those attained with the apparatus and methods disclosed in our previously-referenced patent application wherein inspection signals are only compared with data that pertains to or defines an identically configured flaw-free structure. For example, one of the problems that can be encountered both with prior art CW eddy current inspection arrangements and arrangements configured in accordance with our previously-mentioned patent application is that it can be difficult to distinguish between inspection signals which indicate the presence of a subsurface crack or flaw and inspection signals which result from an air gap or other spacing between the surface of the structure being inspected and the inspection system excitation and sensing coils (e.g., drive coil 12 and pick-up coil 26 of the arrangement depicted in FIG. 1). Such spacing or "lift-off" is especially important relative to the inspection of multilayer aircraft structure and other such arrangements in that a surface coating of paint or other protective dielectric substance is often utilized. Generally, the lift-off caused by the protective coating such as the dielectric coating 32 of FIG. 1 (and/or improper positioning of drive coil 12 and pick-up coil 26) is not controlled during either manufacture or maintenance of the aircraft and heretofore has sometimes resulted in somewhat ambiguous inspection results, especially when both lift-off and a relatively small subsurface crack or flaw are present.

The potential inspection signal ambiguities that can be encountered with our above-mentioned previous inspection techniques can be understood with reference to FIG. 2B, which depicts signal waveforms 34, 36 and 38 that respectively represent three different conditions relative to flaws and lift-off in a particular structure being inspected and the inspection arrangement. In particular, waveform 34 represents the signal supplied by pick-up coil 26 when a flaw-free reference specimen (i.e., a structure that exhibits nominal design values relative to all dimensions and material properties that affect the structure electromagnetic properties) is inspected in the arrangement of FIG. 1 and no lift-off or dielectric coating 32 is present. As was previously mentioned, a signal corresponding to waveform 34 (hereinafter referred to as a "flaw-free, no lift-off reference signal") is utilized in the apparatus and methods disclosed in our previously-referenced patent application to provide a reference or basis for evaluating the inspection signals obtained when identically configured fastener regions are inspected for cracks or other subsurface flaws. For example, waveform 36 of FIG. 2B illustrates the signal supplied by pick-up coil 26 when a substantial crack of approximately 0.5 inches in length extends substantially through the entire thickness of the metal layer corresponding to bottom sheet 18 in FIG. 1 and no lift-off is present. In accordance with the method and apparatus of our referenced patent application the maximum signal amplitudes of flaw-free, no lift-off reference signal 34 and inspection signal 36 are compared to the presence of the flaw, e.g., the difference in the maximum amplitude attained by the reference signal 34 and the inspection signal 36 ($\Delta A_1 = A_0 - A_1$ in FIG. 2B) is utilized as an indication that a subsurface flaw is present.

Although comparison of the maximum amplitude of a single reference signal with the maximum amplitude of individual inspection signals obtained when identically configured portions of aircraft or other manufactured structure is inspected with the arrangement of FIG. 1 may be satisfactory in locating rather large subsurface flaws, some difficulty can be experienced relative to distinguishing between smaller subsurface flaws and inspection signals that result because of a dielectric layer 32 or other types of lift-off. In particular, waveform 38 of FIG. 2B illustrates the inspection signal that results when the reference specimen providing the reference signal 34 is spaced apart from the drive coil 12 and sensing coil 26 of FIG. 1 by an air gap or paint layer as thin as 0.010 inches (approximately 0.254 millimeters). As can be clearly seen in FIG. 2B, the maximum amplitude of this "lift-off only" signal ($A_2$) is greater than the maximum amplitude of flaw-free, no lift-off reference signal 34 ($A_0$) and is substantially greater than the maximum amplitude of signal 36 ($A_1$), which results due to a large subsurface flaw and no lift-off. Further, signal 38 attains maximum amplitude at a time denoted as $t_7$ in FIG. 2B, which is less than the time at which the reference signal 34 reaches maximum amplitude ($t_5$) and $t_5$ is less than the time required for inspection signal 36 to reach maximum amplitude (time $t_6$). Although the three signals depicted in FIG. 2B can be clearly distinguished from one another on the basis of above-noted differences in maximum signal amplitude, the inspection signals resulting from much smaller subsurface flaws and from subsurface flaws that must be located in the presence of lift-off can exhibit a signal amplitude which, standing alone, does not reliably indicate the condition of the structure under test. In this regard, although experience to date indicates that all lift-off signals are greater in magnitude and exhibit a lower time value than the associated flaw-free, no lift-off reference signal, no general relationship has been observed relative to a "crack-only" signal such as signal 36 of FIG. 2B. In fact, it has been found that a subsurface crack or flaw can result in either an increase or a decrease in the maximum amplitude of the inspection signal and that the associated time value (the time required to reach maximum amplitude) can be either greater than or less than the time value associated with a flaw-free, no lift-off reference signal. Because of such variance in the inspection signals obtained from variously configured structure, an inspection signal quite similar to the lift-off only signal 38 of FIG. 2B can be generated by subsurface flaw. For example, it has been observed that cracks which are located relatively deep within the structure (e.g., in a bottom sheet 18 that is covered by a relatively thick surface sheet 16) often result in an inspection signal having an amplitude greater than the reference signal and attaining such amplitude in less time than is required for the reference signal, even when no lift-off is present. Further, the rise time of the excitation signal supplied to drive coil 12 ($t_1 - t_0$ in FIG. 2A) has some effect on the nature of the signal response obtained when a subsurface flaw is present, with longer rise times generally resulting in the signal conditions depicted in FIG. 2B and relatively short rise times being more likely to result in an inspection signal exhibiting a maximum amplitude that exceeds that of the flaw-free, no lift-off reference signal. Because of this variation in inspection signals and because inspection signals which exhibit both lift-off and a subsurface flaw range in maximum amplitude between the value associated with a "worst-case" lift-off only signal (e.g., waveform 38 in FIG. 2B) and a worst-case flaw-only signal (e.g., waveform 36), some subsurface flaws cannot be detected on the basis of inspection signal amplitude alone when lift-off is present.

We have discovered, however, that certain general relationships exist relative to "crack-only" inspection signals and relative to "lift-off only" inspection signals which permit modification or compensation of inspection signal amplitude so as to, in effect, eliminate at least a substantial portion of the situations in which the presence of lift-off causes an ambiguous inspection signal. More specifically, and with reference to FIG. 3, the maximum signal amplitude and associated time characteristic of flaw-free, no lift-off signal 34, crack-only reference signal 36 and lift-off only signal 38 can be represented in a time-amplitude rectangular coordinate system (time-amplitude space) by the depicted points $R_0$, $R_1$ and $R_2$, respectively. Through conducting numerous tests with variously configured multilayer structure, it has been determined that if the size of a crack in a subsurface layer such as bottom sheet 18 of FIG. 1 is the only system variable, the maximum amplitude and associated time characteristic of the signal provided by pick-up coil 26 will substantially correspond to a point on a line that passes through $R_0$ (the flaw-free, no lift-off reference) and $R_1$ (a known or reference crack-only signal). Stated otherwise, we have found that, for each particular structure and for the maximum amplitude and time characteristic of each crack-only signal can be considered to correspond to a point that lies on a straight line passing through the reference points $R_0$ and $R_1$, i.e., a line defined by the expression $A - A_0 = (A_1 - A_0)(t - t_5)/(t_6 - t_5)$ and depicted as line segment 40 in FIG. 3, where, as previously noted, $R_0 = (A_0, t_5)$ defines the maximum amplitude and time characteristic of a flaw-free, no lift-off reference signal (waveform 34 in FIG. 2B) and $R_1 = (A_1, t_6)$ defines the maximum amplitude and time characteristic of a crack-only reference signal (waveform 36 in FIG. 2B).

As is indicated by the straight line segment 42 extending between $R_0$ and $R_2$ in FIG. 3, we have also discovered that a similar parametric relationship exists when lift-off is the only system variable, at least over the range of lift-off that is commonly encountered in the practice of the invention. For example, for the specific multilayer fastener structure associated with FIG. 3, each inspection signal that results when only an unknown amount of lift-off is present will correspond to a point in time-amplitude space which lies on a line $A - A_0 = (A_2 - A_0)(t - t_5)/(t_7 - t_5)$, where $A_0$, $t_5$ and $A_2$, $t_7$ respectively define the points $R_0$ and $R_2$ of FIG. 3 and correspond to the maximum amplitude and time characteristics of flaw-free, no lift-off signal 34 and lift-off only reference signal 38 in FIG. 2B.

As will be recognized by those skilled in the art, if it is assumed that the inspection system is linear relative to signal changes resulting from various combinations of crack size and amount of lift-off, i.e., the superposition applies, each inspection signal that results when both lift-off and a subsurface crack are present will lie within a prescribed region of the time-amplitude space depicted in FIG. 3 and define a point that can be resolved into components that extend along the "crack-only" line segment 40 and "lift-off only" line 42 of FIG. 3. Although the full extent of such assumptions and the underlying principles which allow the assumptions to remain relatively valid over a variable range interest are not completely understood, it has been experimentally determined that the above-discussed linear relationships remain reasonably valid with respect to conventionally configured multilayer arrangements that are joined together by conventional bolts, rivets and other fasteners. In particular, it has been found that inspection system sensitivity and reliability are increased relative to that of the method and apparatus disclosed in our previously-mentioned patent application by processing each inspection signal to, in effect, determine the component of the inspection signal that lies along the crack-only line for the particular structure of interest, e.g., line 40 in FIG. 3, and by utilizing that component to indicate whether or not a subsurface crack is present.

For example and with continued reference to FIG. 3, when the embodiment of FIG. 1 is utilized to inspect aircraft fastener structure which is coated with a layer of paint, and a signal which corresponds to the point $R_n = (A_n, t_n)$ in FIG. 3 is obtained, the time-amplitude parametric relations that define the crack-only line 40 and lift-off only line 42 for that particular multilayer arrangement are utilized in conjunction with the inspection signal amplitude and time information ($A_n$ and $t_n$) to, in effect, determine "crack-only" and "lift-off only" signal components, which (under the above-mentioned assumptions) correspond to the crack and lift-off conditions of the inspection situation being encountered. In this regard, in view of the time-amplitude geometric considerations that are inherent to the above-discussed time-amplitude relationships, various signal processing arrangements and techniques can be utilized, with each such arrangement or technique effectively determining the intersection between crack-only line 40 and a line that passes through the point $R_n$ and exhibits a slope equal to that of the lift-off only line 42. Thus, it can be shown that the amplitude component of the intersection between a line which exhibits the necessary slope and passes through $R_n$ is given, for example, by the expression:

$$A_c = A_0 + \frac{(A_1 - A_0)}{m(t_6 - t_5) - (A_1 - A_0)}[A_0 + m(t_n - t_5) - A_n];$$

where m is the slope of lift-off only line 42, i.e., $m = (A_2 - A_0)/(t_7 - t_5)$.

If desired for signal processing means, this relationship can also be expressed as:

$$A_c = A_0 + \frac{n}{m - n} A_0 + (t_n - t_5) - A_n$$

where n is the slope of the crack-only line 40, i.e., $n = (A_0 - A_1)/(t_0 - t_6)$. Further, it can be recognized the corresponding time characteristic ($t_c$) can be determined simply by substituting the resulting value of $A_c$ into the previously-stated equation that defines crack-only line 40.

As previously mentioned, corrected amplitude information such as the above-discussed value $A_c$ has proven to be a sufficient indication of the presence of a subsurface crack or flaw and the presently preferred embodiments of the invention do not process inspection signals so as to determine the associated time characteristic, $t_c$. Further, in the presently preferred embodiments of the invention which utilize digital signal analysis and other situations, it can be advantageous to minimize the magnitude of the amplitude and time values utilized in determining the corrected inspection indication and also to minimize the amount of signal information necessary to define the appropriate crack-only and lift-off only line segments (lines 40 and 42 in FIG. 3). In this regard, it can be recognized that translation of the depicted coordinate system so that the origin of the transformed coordinate space is determined by the flaw-free, no lift-off reference signal (i.e., corresponds with $R_0 = (A_0, t_5)$ in FIG. 2B) minimizes the number of parameters necessary to define crack-only line 40 and lift-off only line 42 and also reduces the magnitude of both the time and amplitude values. In particular, when the maximum amplitude and associated time component of the flaw-free, no lift-off reference signal is used to define the origin of the time-amplitude coordinate space, only one parameter associated with each of the lines 40 and 42 is required to define the necessary reference information for any given multilayer structure. Moreover, the magnitude of the coordinates associated with both $R_1$ and $R_2$ in the transformed coordinate system are less than the corresponding quantities in the original system in that $R_{1t} = (\Delta A_1, \Delta t_1)$ and $R_{2t} = (\Delta A_2, t_2)$, where t designates the transformed coordinate system, the reference point $R_1$ in FIG. 3 is given by the expression $\Delta A_1 = A_1 - A_0$, $\Delta t_1 = t_6 - t_5$, $\Delta A_2 = A_2 - A_0$ and $\Delta t_2 = t_2 - t_5$. Substituting these expressions into the previously set forth equation for the compensated inspection signal and utilizing the difference between the maximum amplitude of the flaw-free, no lift-off reference signal and the maximum amplitude of the corrected or compensated signal ($\Delta A_c = A_c - A_0$) as an indication of the presence of a subsurface crack or flaw yields:

$$\Delta A_c = \frac{\Delta A_1}{m\Delta t_1 - \Delta A_1}[m\Delta t_n - \Delta A_n];$$

where $\Delta t_n = t_n - t_5$ and $\Delta A_n = A_n - A_0$.

Various alternative expressions are available which may facilitate the particular signal processing utilized within a given embodiment of the invention. For example, utilizing the slope of crack-only line 42 (i.e., $n = (A_0 - A_1)/(t_0 - t_1)$) allows the compensated amplitude value to be expressed as $$\Delta A_c = n(m\Delta t_n - \Delta A_n)/(m-n).$$

Regardless of whether the present invention is practiced with one of the previously set forth expressions for the compensated amplitude value or through the use of some other equivalent expression, the procedure employed in the above-discussed eddy current inspection technique can be summarized by briefly reviewing the reference information required for each particular structure of interest and the basic signal processing that is employed to provide the lift-off compensated indication that a subsurface flaw or discontinuity is present. With respect to the required reference data, various techniques can be employed to determine the crack-only and lift-off only reference lines in the time-amplitude coordinate space of FIG. 3, a procedure utilizing three separate eddy current inspection signals is employed in the presently preferred embodiments of the invention. In this procedure, a flaw-free reference specimen substantially identical in configuration to the multilayer arrangement to be inspected is utilized to provide the flaw-free, no lift-off reference signal (e.g., signal 34 in FIG. 2B); a dielectric spacer is inserted between the flaw-free reference specimen and the inspection system excitation and pick-up coils (drive coil 12 and pick-up coil 26 in FIG. 1) and the inspection system is activated so as to provide a signal that can be utilized for the lift-off only reference signal (signal 38 in FIG. 2B); and a crack-only reference signal (e.g., signal 36 in FIG. 2B) is determined by operating the inspection system in conjunction with a second reference specimen which, with the exception of a known subsurface flaw, is identically configured to the structure to be inspected.

With the crack-only and lift-off only lines defined by the three above test sequences or in some other way, the actual inspection signals are processed to, in effect, determine the amplitude component of a point defined by the intersection of the crack-only line and a line which passes through the point in time-amplitude space which is defined by the inspection signal and which exhibits a slope identical to that of the lift-off only line. As will be recognized by those skilled in the art, both the above-described sequence for determining the required reference data and the signal processing necessary in order to determine the compensated flaw indication can be readily implemented by use of either analog or digital circuit arrangements. As shall be described in the following paragraphs, the presently preferred embodiments of the invention use digital signal processing that is controlled and implemented by a microprocessor or other programmable sequential machine since such an arrangement permits storage of the reference signal information for a relatively large number of multilayer conductor arrangements and further permits inclusion of a number of options that can improve system operation.

With an understanding of the more conceptional aspects of the compensation effected in accordance with the invention, the arrangement and function of signal supply unit 20 and display and analysis unit 30 can be readily understood. In this regard, those skilled in the art will recognize that a variety of circuit arrangements can be employed to generate an inspection system excitation current which corresponds to the previously-discussed waveform 25 of FIG. 2A. As is depicted in FIG. 1, one convenient arrangement, which generally corresponds to the portable power supply disclosed in U.S. Pat. No. 4,148,091 which issued on Apr. 3, 1979 and is assigned to the assignee of this invention, includes first and second capacitor banks (46 and 48) which are selectively discharged through drive coil 12 by means of logic-controlled switches 50 and 52. More specifically, in the depicted signal supply unit 20, capacitor bank 46 and capacitor bank 48 are respectively charged by chargers 54 and 56 prior to the initiation of each current pulse. A ratio control circuit 58, interconnected with chargers 54 and 56, controls the voltage to which capacitor banks 46 and 48 are charged so that the desired values of maximum and minimum current will be attained ($I_{max}$ and $I_{min}$ in FIG. 2B).

To initiate each excitation current pulse 25, a switching control unit 60 closes switch 50 so that capacitor bank 46 discharges through drive coil 12 via electrical connections 22 and 24. For example, switch 50 can be a conventional manually-operated switch which completes the indicated circuit path and simultaneously energizes switching logic 60 for subsequent activation of switch 52. A blocking inductor having an inductance value which results in the desired rise time, is connected in series between capacitor bank 46 and drive coil 12. As the excitation current 25 reaches $I_{max}$ (or shortly thereafter), switching control 60 closes switch 52 to discharge capacitor bank 48 through drive coil 12 with the current supplied by capacitor bank 48 being opposite in polarity relative to that current supplied by capacitor bank 46. Thus, activation of switch 52 causes the current through drive coil 12 to rapidly decrease with a resistor 64, connected in series with capacitor bank 48 and drive coil 12 establishing the fall time of excitation current 25. Those skilled in the art will recognize that various conventional circuit arrangements can be utilized in switching control unit 60 to cause the activation of switch 52 in the above-described manner. For example, switching control 60 can include conventional timing circuits that activate switch 52 a predetermined time after the activation of switch 50 or can include circuitry for detecting the time at which excitation current 25 reaches $I_{max}$.

Turning now to the provisions of FIG. 1 which relate to determining the maximum amplitude and associated time characteristic of each inspection signal provided by pick-up coil 26 and implementing the above-described compensation for lift-off, the depicted display and analysis unit 30 includes a selector switch 68 that is configured and connected so as to permit selection of a desired electrical tap of pick-up coil 26. In this regard, although selector switch 68 is symbolically represented in FIG. 1 as a conventional manually-operated rotary switch having the wiper arm connected to the input terminal of an amplifier stage 70 and each selector contact thereof connected to an individual electrical tap of pick-up coil 26, it will be recognized that a variety of conventional analog and digital semiconductor circuits can be utilized. In any case, amplifier stage 70 couples the signals provided by pick-up coil 26 to the input port of an analog-to-digital converter (A/D)72. As is indicated in FIG. 1, A/D converter 72 is of the type which provides a parallel format digitally-encoded signal representative of the amplitude of the applied analog signal (the signal supplied by pick-up coil 26) each time a clock pulse is applied to the terminal 74 of FIG. 1. Thus, when a periodic clock signal is provided to the terminal 74, A/D converter, in effect, operates as a sample and hold arrangement, supplying a sequence of digitally-encoded words that corresponds to a sampled data representation of the inspection signal supplied by pick-up coil 26. To ensure that adequate signal information is provided relative to the full range of inspection signals that can be encountered in the practice of the invention, clock or sampling rates on the order of 500 kilohertz are presently employed and each inspection signal is sampled for approximately two milliseconds. Although various arrangements can be utilized for providing the sampling or clock signal to A/D converter 72, the present embodiments of the invention that utilize a microprocessor arrangement typically utilize the crystal-controlled clock circuit contained in such a microprocessor along with appropriate frequency dividers (counter circuits) and time delay networks.

With continued reference to FIG. 1, the depicted display and analysis unit 30 includes a digital signal processor 76 that is sequenced so as to facilitate the previously-discussed determination and storage of inspection signal reference data and to provide the logical and computational operations necessary in compensating the inspection signal in the manner described relative to FIGS. 2 and 3. Various arrangements can be employed for digital signal processor 76, ranging from a rather large general purpose computer that is programmed with software techniques to a specifically designed circuit that utilizes conventional logic elements such as gates, flip-flops and combinational logic elements, with the presently employed embodiments of the invention utilizing a conventional arrangement of integrated circuits that is commonly called a microprocessor. As is depicted in block diagram form in FIG. 1, such a microprocessor generally includes a central processing unit (CPU) 78, a programmable read-only memory (PROM) 80, a random access memory (RAM) 82 and an input-output (I/O) unit 84.

In operation, PROM 80 is programmed with the various operating instructions and nonvolatile data necessary for performing the desired computational sequences. CPU 78 accesses the required input signals (i.e., the digitally-encoded inspection signal provided by A/D converter 72) via the I/O 84 in accordance with the instructions stored in PROM 80 and, utilizing storage registers within RAM 82 as a "scratch pad memory", performs the necessary arithmetic and logic operations (e.g., determines the compensated signal that indicates the presence of a subsurface flaw). As is further indicated in FIG. 1, I/O unit 84 couples the test indication signal (e.g., the digitally-encoded compensated signal provided by RAM 82 via CPU 78) to an amplitude display unit 86, which can include a suitable number of seven-segment alphanumeric indicators formed with liquid crystal elements or other devices such as light-emitting diodes. A second display unit 88 for indicating the time coordinate associated with the displayed amplitude coordinate can be included if desired, to, for example, provide the test set operator with additional information about each inspection signal.

To provide an interface between the test set operator and digital signal processor 76, the arrangement of FIG. 1 includes a mode selector 90 which supplies a parallel format digitally-encoded signal to the microprocessor I/O unit 84 that allows the test set operator to control operation of the inspection system and select various test options that can easily be made available by suitably configuring digital signal processor 76 (microprocessor). As is symbolically depicted in FIG. 1, one simple and convenient way of providing a parallel format mode selection signal is by use of a series of single pole switches 92 that are manually operated to establish the logic level of each bit within the supplied digital word.

Figure 4:
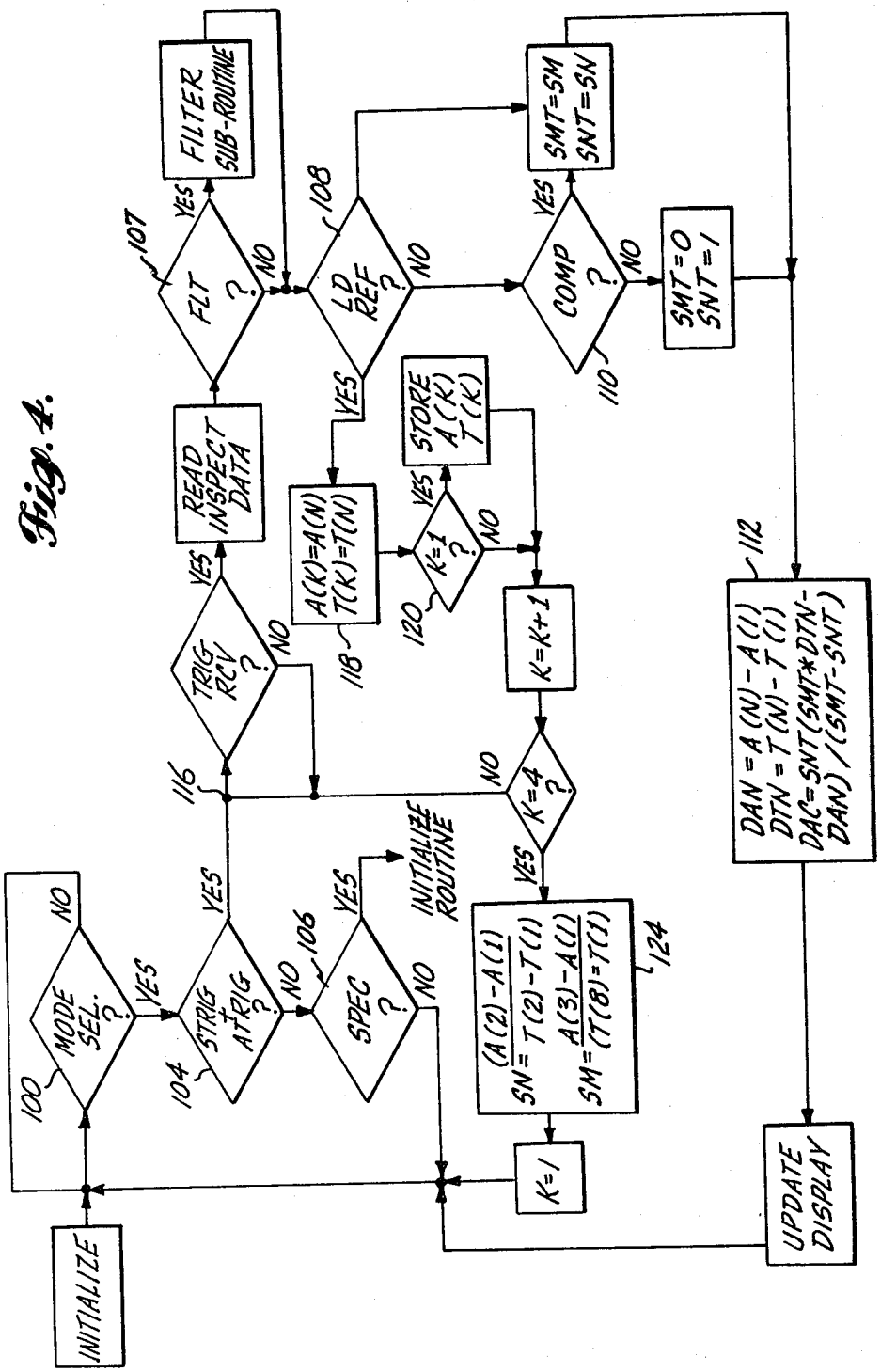
FIG. 4 is a flow diagram which illustrates the manner in which the digital processing unit that is utilized in the invention is sequenced in order to provide an inspection indication that is compensated for lift-off or another selected system variable.

An example of the manner in which mode selector 90 and a microprocessor realization of digital signal processor 76 can be configured and arranged to facilitate the practice of the invention and, in addition, provide various test options can be considered with reference to FIG. 4, which illustrates an operational sequence or flow chart applicable to one embodiment of the invention. In this particular embodiment, mode selector 90 is configured to couple a parallel format digital signal to the I/O 84 of digital signal processor 76 which is encoded to select: (1) operation in either an "autotrigger" mode wherein each inspection signal of a sequence of inspection signals produced by pick-up coil 26 is processed and displayed or a "single trigger" mode wherein analysis and display unit 30 processes the next-most inspection signal supplied by pick-up coil 26 and then reverts to a standby condition; (2) operation in either a compensated mode wherein digital signal processor 76 implements the previously-described compensation or in an uncompensated mode wherein digital signal processor 76 causes the inspection system to operate in the manner described in our previously-referenced patent application; (3) operation in a "load reference" mode wherein the digital signal processor 76 determines the previously-described flaw-free, no lift-off reference information, the crack-only information and the lift-off only information from inspection signals that are provided when appropriate reference specimens are utilized in the inspection system; (4) activation of a "filter" mode that can be used in conjunction with compensated or uncompensated operation of the depicted embodiment in either the autotrigger or single trigger modes to digitally filter the inspection signal being processed in a manner which corresponds to minimum phase low-pass analog filtering of the signal supplied by pick-up coil 26; and (5) operation of the microprocessor in a "special" mode which, for example, can be utilized for accessing and displaying the data stored within each register of PROM 80, or initiating various other maintenance and troubleshooting routines (e.g., a "self-test") that are well-known to those skilled in the art.

With more particular reference to FIG. 4, digital signal processor 76 is initialized to set various computational parameters discussed in the following paragraphs equal to zero (or some other desired initial value) each time the inspection system is energized or reset. Upon completion of the initialization sequence, CPU 78 of FIG. 1 accesses the parallel format digital word that is supplied by mode selector 90 via I/O unit 84 to determine the selected mode of operation. For example, each of the operational modes provided by the arrangement of FIG. 4 can be represented by separate binary coded decimal signal (or by a logical 1 in a particular bit of the digital signal) and a "standby" mode can be initiated when each bit within the digital signal is equal to a logical zero. In any case, as is indicated by the decisional block 100 in FIG. 4, the digital signal processor continues to periodically access the digitally-encoded mode selection signal and, when an appropriately coded signal is present, operates to determine whether or not mode selector 90 is set to either the autotrigger or single trigger mode. For example, as is indicated by decisional block 104 of FIG. 4, the digital processing arrangement can be sequenced so as to perform a conventional logical OR operation with two variables that are contained in (or determined from) the mode selection signal and represent selection of the autotrigger mode and the single trigger mode (denoted ATRIG and STRIG, respectively in FIG. 4). If neither of these modes has been selected, the signal processor operates so as to determine whether a special function has been selected (indicated by decisional block 106 in FIG. 4). If a special mode of operation such as a troubleshooting or maintenance routine has been selected, the digital signal processor is then sequenced according to that routine. On the other hand, if a special mode has not been selected, the digital signal processor advances to the beginning of the depicted signal processing sequence to await an appropriate mode selection signal.

If (during operation of the digital signal processor which corresponds to decisional block 104) it is determined that either the autotrigger or single trigger mode have been selected, the digital signal processor sequences so as to process the next inspection signal that is supplied by pick-up coil 26. For example, as is indicated in FIG. 4, a trigger signal (TRIG), which is supplied by signal supply unit 20 of FIG. 1, can be used to activate the digital signal processor so that the sequence of digital signals that is provided by A/D converter 72 in the previously-discussed manner is read into system memory.

With data stored that represents the inspection signal supplied by pick-up coil 26, the digital signal processor next determines whether mode selector 90 is operated to select the filter mode of operation (decisional block 107 in FIG. 4). If signal filtering is to be effected, the digital signal processor is then sequenced with a subroutine appropriate to the desired filter function. In this regard, it will be recognized that various digital filtering operations can be advantageous in the practice of the invention. For example, a filtering or data smoothing technique commonly identified as "n-point averaging" is utilized in one realization of the invention to, in effect, low-pass filter each inspection signal without altering the time or phase characteristic. When such a filtering sequence is complete, or if the filtered mode has not been selected, the digital processor is then operated so as to determine whether or not inspection reference signals are to be supplied by pick-up coil 26 and stored within system memory for subsequent inspection sequences. In FIG. 4, this operation is indicated by the decisional block 108 which determines the logical state of a variable denoted as LDREF which, like the other mode selection variables utilized in the depicted sequence, can be one bit of the supplied mode selection signal or a computational parameter ("flag") that is set on the basis of the mode selection signal.

Assuming that the necessary reference information has already been loaded into digital signal processor 76, i.e., that the previously-described crack-only reference signal, lift-off only reference signal, and flaw-free, no lift-off reference signal that pertain to the structure to be inspected have been supplied to digital signal processor 76 and appropriate reference parameters have been entered into memory registers of PROM 80, the sequence of FIG. 4 then determines whether operation in the compensation mode has been selected (decisional block 110 of FIG. 4). If the system is not being operated in the compensated mode (i.e., uncompensated time and/or amplitude information is being utilized as an indication of a subsurface flaw), a computational variable SMT is set equal to zero and a second computational variable SNT is set equal to 1 and the system sequences to a series of computations indicated at block 112 of FIG. 4. If the system is being operated in the compensated mode the variables SMT and SNT are set equal to SM and SN, which as described hereinafter respectively correspond to the slopes of lift-off only line 42 and crack-only line 40 of FIG. 3. As shall also be described hereinafter, the slopes (SM and SN) are determined and stored during the operation of the system in the "load reference" mode.

The computational expressions of block 112 correspond to the previously set forth equation that expresses the compensated amplitude value in terms of the slopes of lines 40 and 42 of FIG. 3, the difference between the amplitude of the flaw-free, no lift-off reference signal and the inspection signal being processed and the time difference between these two signals. Further, because of the above-described initialization of computational variables SMT and SNT, the computational sequence set forth at block 112 results in the appropriate compensated or uncompensated inspection signal indications. More specifically, in the procedure defined by block 112 the variable DAN corresponds to $\Delta A_n$, the variable DTN corresponds to $\Delta t_n$ and the variable DAC corresponds to $\Delta A_c$ (the compensated inspection indication). The digital signal processor 76 determines the differential amplitude (DAN) and corresponding differential time characteristic (DTN) from the stored digital representation of the inspection signal by sequentially testing each stored amplitude signal to determine the maximum amplitude; multiplying the number of stored signal samples that preceed the maximum amplitude signal by the period of the clock which drives A/D converter 72 to obtain the relative time at which the inspection signal reaches maximum amplitude; and subtracting the maximum amplitude of the flaw-free, no lift-off reference signal (A(1)) and the associated time (T(1)) from the amplitude and time values that apply to the inspection signal being processed (A(N) and T(N) in FIG. 4). The inspection system indicator signal (DAC) is then computed with the computation set forth in block 112 corresponding to the previously-set forth equation for $\Delta A_c$. However, if it was determined at decisional block 110 that the system is operating in an uncompensated mode, the values of SMT and SNT utilized will cause DAC to be identically equal to the maximum amplitude of the inspection signal being processed minus the maximum amplitude of the flaw-free, no-crack reference signal. Hence, as previously mentioned, decisional block 110 in conjunction with the computational process of block 112 results in either a compensated or an uncompensated inspection indication, as determined by the mode selection signal. In either case, the inspection indication obtained by the procedure of block 112 and, if desired, the associated maximum amplitude and time values are utilized to update the system display units (86 and 88 in FIG. 1). The signal processor then recycles to the indicated point at which it continues to determine the status of the mode selection signal until further action is required.

As previously mentioned, decisional block 108 of the sequence of FIG. 4 initiates the load reference mode of operation to store appropriate reference information, i.e., the maximum amplitude and associated time of the flaw-free, no lift-off reference signal (A(1) and T(1) in the sequence of FIG. 4) along with the slopes (SM and SN) that define the lift-off only and crack-only lines (42 and 40 in FIG. 3). In the particular load reference sequence that is illustrated in FIG. 4, the flaw-free, no lift-off reference data is loaded first, the lift-off only data is loaded second, and the crack-only reference data is loaded last, with a logic variable denoted as K in FIG. 4 controlling the computational sequence to properly process and store the reference information. In this regard, K is initially equal to 1 so that, as is indicated by the computational steps in block 118 of FIG. 4, A(1) is set equal to the maximum amplitude of the inspection signal currently stored in system memory (i.e., the flaw-free, no lift-off reference signal) and T(1) is set equal to the corresponding time. As is indicated by decisional block 120, A(1) and T(1) are then stored for subsequent use in the previously discussed determination of the compensated or uncompensated inspection signal indication. Next, the variable K is incremented by 1 and tested to see if the incremented value is equal to 4 (i.e., tests that determine whether all three reference signals have been processed). If K is not equal to 4 the load reference mode has not been completed and the signal processing unit recycles to the point in the signal processing diagram of FIG. 4 denoted by the numeral 116 to await the next reference signal. In this regard, when K is equal to 2 the system will be ready to receive and process the lift-off only signal and when K is equal to 3 the system is prepared for the crack-only reference signal. On the other hand, if K is equal to 4 the amplitude and time information is available for all three reference signals and the slopes of the lift-off only and crack-only lines (FIG. 3) are determined through implementation of computations identical to those described relative to FIG. 3 (block 124 in FIG. 4 wherein the lift-off only and crack-only slopes are denoted as SM and SN, respectively). If all reference data necessary for the particular multilayer structure being inspected has been determined SM and SN are stored in system memory, K is set equal to 1 and digital signal processor recycles to decisional block 100.

It will be recognized by those skilled in the art that the embodiments of the invention described herein are exemplary in nature and that various changes and modifications can be made without exceeding the scope and the spirit of the invention. In this regard and as previously mentioned, various signal processing arrangements and sequences can be utilized. Further, the invention is not limited to compensation of an eddy current signal for variation in lift-off or any other single variable that affects the inspection system electromagnetic environment. In this regard, and with reference to FIG. 5, it has been found that inspection system parameters other than crack size and lift-off, in effect, lie on or define straight lines in the herein described time-amplitude space. For example, as is clearly shown in FIG. 5, it has been determined that variation in spacing or gap between layers of the multilayer structure (i.e., between surface sheet 16 and bottom sheet 18 of FIG. 1) defines a relatively straight line (denoted by the numeral 130 in FIG. 5) which is similar to the line defined by variation in lift-off only (e.g., lift-off only line 40 of FIG. 3). As is also indicate by the line segment indicated by the numeral 132, edge margin (distance) between fastener 14 and the boundary edge of top sheet 16 in FIG. 1) exhibits similar characteristics. Thus, it can be recognized that the compensation method and apparatus of the invention can be utilized to compensate for a variable such as spacing between conductive layers or fastener edge margin, if desired or necessary. Further, it can be noted that an embodiment of the invention that is configured to compensate for edge margin, spacing or lift-off will, in fact, improve system performance when the other variable is encountered. That is, because of the similarity between the lift-off only characteristics (line 40 of FIG. 3) and the spacing only and edge margin characteristics (lines 130 and 132 of FIG. 5, respectively) at least partial compensation occurs when compensation is based on a particular one of the lines and variation occurs in another system parameter which is described by the other line in inspection signal time-amplitude space.

Figure 5:
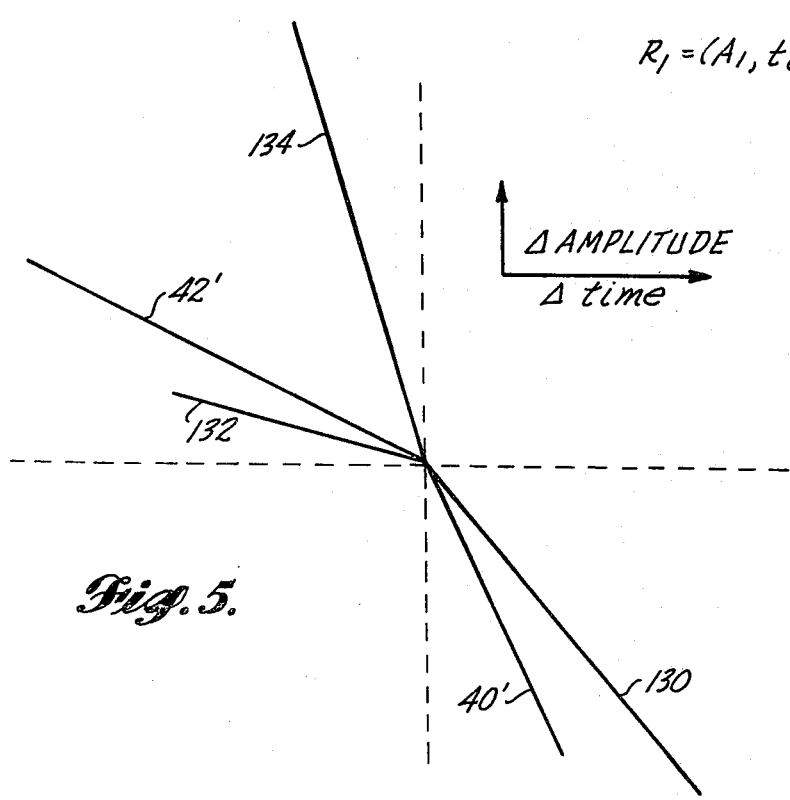
FIG. 5 graphically illustrates the amplitude-time characteristics associated with variation in fastener edge margin, variation in fastener height or protrusion above the surface of the multilayer structure, and the presence of a gap or spacing of various magnitude between adjacent layers of the multilayer structure.

As is also indicated in FIG. 5 by a line denoted by the numeral 134, variation in the protrusion of high permeability fasteners (e.g., steel) above the surface of a relatively low permeability structure (e.g., aluminum or titanium) also appears to define a relatively straight line in time-amplitude space. Accordingly, although fastener protrusion is generally visibly observable and of considerably less concern than variations in parameters such as lift-off, the subject invention can be configured to compensate for variations in fastener protrusions by utilizing an appropriate reference structure and implementing suitable minor modification of the herein described methods and apparatus.

The embodiments of the invention in which an exclusive property or privilege is claimed are defined as follows:

1. An eddy current inspection system for detecting the presence of subsurface regions within a body wherein the region to be detected is of a different electrical conductivity than portions of said body that surrounds said region to be detected, said eddy current inspection system comprising:

drive coil means positionable on the surface of said body to be inspected, said drive coil means being configured for inducing a magnetic field that is directed inwardly into an inspected region of said body in response to an applied drive signal;

electrical signal supply means interconnected with said drive coil for supplying said drive signal, said electrical signal supply means including means for supplying said drive signal as a current pulse having a relatively long rise time and a substantially shorter fall time;

magnetic flux detection means positionable on said surface of said body being inspected at a location proximate to said drive coil means, said magnetic flux detection means for supplying an inspection signal representative of the eddy currents produced in said body subsequent to that portion of said drive current exhibiting said short fall time; and analysis and display means for indicating the presence of a subsurface region of different continuity, said analysis and display means connected for receiving said inspection signal supplied by said magnetic detection means, said analysis and display means including signal compensation means for compensating each said inspection signal for variations in a selected inspection system characteristic that affects the electromagnetic environment of said eddy current inspection system, said signal compensation means including means for compensating said inspection signal on the basis of first and second parametric relationships, said first parametric relationship being determined by the maximum amplitude of inspection signals supplied by said magnetic flux detection means when a subsurface region's of different electrical conductivity is present, said second parametric relationship being determined by the maximum amplitude of inspection signals supplied by said magnetic flux detection means when variations in said selected inspection system characteristic are known to be present.

2. The eddy current inspection system of claim 1 wherein said signal compensation means includes means for determining a first amplitude difference that is equal to the difference between the maximum amplitude of each current inspection signal and a first reference signal that is supplied by said flux detection means when said drive coil means is positioned over flaw-free structure substantially identical to the region of said body supplying said current inspection signal, said analysis and display means including means for determining second and third difference signals that are respectively equal to the difference between the maximum amplitude of said first reference signal and second and third reference signals, said second and third reference signals being respectively supplied by said magnetic flux detection means when said drive coil means is positioned over structure that is substantially identical to said region supplying said current inspection signal except for the inclusion of a known subsurface region of different electrical conductivity and a signal supplied by said magnetic flux detection means when said drive coil means is positioned over structure substantially identical to said region supplying said inspection signal except for the inclusion of a known variation in said inspection system characteristic being subjected to compensation, said analysis and display means further including means for determining the time at which said inspection signal and said first, second and third reference signals reach maximum amplitude relative to a predetermined point of time in the associated drive signal supplied by said electrical signal supply means.

3. The eddy current inspection system of claim 2 wherein said indication of a region of different conductivity is substantially defined by the expression $\Delta A_c = n(m\Delta t_n - \Delta A_n)/(m-n)$, where n is equal to the difference between the maximum amplitudes of said third and first reference signals divided by the difference in the time required for said third and first reference signals to reach maximum amplitude, m equals the difference between said maximum amplitudes of said second and first reference signals divided by the difference in time required for said second and first reference signals to reach maximum amplitude, $\Delta t_n$ is equal to the difference in time required for said first reference signal and said inspection signal to reach maximum amplitude, and $\Delta A_n$ is equal to the difference between the maximum amplitude of said inspection signal and said first reference signal.

4. The inspection system of claim 3 wherein said signal analysis and display means includes a digital signal processor having memory means for storing values representative of said first, second and third reference signals, said digital signal processor means including means for accessing said stored values and determining said compensated inspection signal indicator each time said flux detector means supplies an inspection signal.

5. The eddy current inspection system of claims 1, 2, 3 or 4 wherein said drive coil is a solenoidal coil and said flux detection means is a spirally-wound pancake coil mounted to one face of said solenoidal drive coil, said solenoidal drive coil and said pancake pick-up coil being dimensioned and arranged for detecting subsurface flaws surrounding fasteners that join multilayer conductive structure.

6. A method for detecting subsurface flaws within a conductive body comprising the steps of:
inducing a slowly rising magnetic field into a region of said conductive body that is to be examined for said subsurface flaws with the lines of said magnetic flux extending inwardly into said conductive body;
rapidly collapsing said induced magnetic field to generate substantial eddy currents which circulate through said region of said conductive body being examined;
monitoring the magnetic field variations caused by said eddy currents to supply a detection signal representative of the magnetic field variations caused by said eddy currents;
determining a first difference signal by comparing said detection signal with a first reference signal which results when said induced magnetic field is introduced into a flaw-free conductive body having substantially the same geometry as said region of said conductive body being examined;
determining a second difference signal by comparing said first reference signal with a second reference signal which results when said induced magnetic field is introduced into a flaw-free conductive body having substantially the same geometry as said region of said conductive body being examined and said method is conducted to introduce a known variation in a parameter known to affect the electromagnetic environment that determines said magnetic field variations caused by said eddy currents;
determining a third difference signal by comparing said first reference signal with a third reference signal which results when said induced magnetic field is introduced into a conductive body having substantially the same geometry as said region of said conductive body being examined and having a known subsurface flaw; and
combining said first, second and third difference signals to produce a flaw indication that is compensated for variations in said inspection system characteristic that may be present.

7. The method of claim 6 wherein:
the step of determining said first difference signal includes the steps of detecting the maximum amplitude of said first reference signal and the time at which said first reference signal reaches said maximum amplitude relative to a predetermined time in the step of inducing said slowly rising magnetic field and collapsing said induced magnetic field, detecting the time at which said detection signal reaches maximum amplitude and the time at which said detection signal reaches said maximum amplitude, determining the difference between the maximum amplitude of said detection signal and said first reference signal, and determining the difference in time required for said detection signal and said first reference signal to reach said maximum amplitudes;

the step of determining said second difference signal includes the steps of detecting the maximum amplitude of said second reference signal and the time at which said second reference signal reaches maximum amplitude, determining the difference between said maximum amplitudes of said first and second reference signals, and determining the difference in time required for said first and second reference signals to reach maximum amplitude; and wherein said step of determining said third difference signal includes the step of determining the maximum amplitude of said third reference signal, detecting the time at which said third reference signal reaches said maximum amplitude, determining the difference between said maximum amplitudes of said first and third reference signals and determining the difference in time required for said first and third reference signals to reach maximum amplitude.

8. The method of claim 7 wherein said step of combining said first, second and third difference signals to produce said compensated flaw indication comprises combining said difference signals in a manner that substantially corresponds with the expression $n(m\Delta t_n - \Delta A_n)/(m-n)$, where m represents said difference between said maximum amplitudes of said first and second reference signals divided by said difference in time required for said first and second reference signals to reach maximum amplitude, n equals said difference between said maximum amplitudes of said first and third reference signals divided by the difference in time required for said first and third reference signals to reach maximum amplitude, $\Delta_n$ denotes the difference in time required for said detection signal and said first reference signal to reach maximum amplitude and $\Delta A_n$ is equal to said difference between said maximum amplitudes of said first reference signal and said detection signal.

* * * * *

UNITED STATES PATENT AND TRADEMARK OFFICE
CERTIFICATE OF CORRECTION

PATENT NO. : 4,383,218

DATED : May 10, 1983

INVENTOR(S) : Hansen et al.

It is certified that error appears in the above-identified patent and that said Letters Patent is hereby corrected as shown below:

Abstract, line 6, "last" should be --fast--

Abstract, line 12, after "pick-up" insert --coil--

Column 1, line 45, "dicloses" should be --discloses--

Title, in [54], "FLOW" should be --FLAW--

*Signed and Sealed this*

*Twenty-sixth* Day of *June 1984*

[SEAL]

Attest:

Attesting Officer

GERALD J. MOSSINGHOFF

*Commissioner of Patents and Trademarks*